(12) United States Patent
Satou

(10) Patent No.: US 6,497,715 B2
(45) Date of Patent: Dec. 24, 2002

(54) ULTRASONIC HAND PIECE AND ULTRASONIC HORN FOR USE WITH THE SAME

(75) Inventor: Yuichirou Satou, Kawasaki (JP)

(73) Assignee: Miwatec Incorporated, Kawasaki (JP)

( * ) Notice: Subject to any disclaimer, the term of this patent is extended or adjusted under 35 U.S.C. 154(b) by 0 days.

(21) Appl. No.: 09/802,813

(22) Filed: Mar. 9, 2001

(65) Prior Publication Data

US 2002/0103497 A1 Aug. 1, 2002

(30) Foreign Application Priority Data

Nov. 7, 2000 (JP) .......................... 2000-338488

(51) Int. Cl.⁷ ................................. A61B 17/32

(52) U.S. Cl. ......................... 606/169; 604/22

(58) Field of Search ................. 606/169, 170, 606/171; 604/22, 35

(56) References Cited

U.S. PATENT DOCUMENTS

| | | | | |
|---|---|---|---|---|
| 5,047,043 A | * | 9/1991 | Kubota et al. | 606/169 |
| 5,151,099 A | * | 9/1992 | Young et al. | 606/169 |
| 5,324,299 A | * | 6/1994 | Davison et al. | 606/167 |
| 5,449,370 A | * | 9/1995 | Vaitekunas | 604/22 |
| 5,674,235 A | * | 10/1997 | Parisi | 604/22 |
| 6,283,981 B1 | * | 9/2001 | Beaupre | 606/169 |

FOREIGN PATENT DOCUMENTS

| | | | |
|---|---|---|---|
| JP | 08275952 | * | 10/1966 |
| JP | 07255736 | * | 10/1995 |
| JP | 10295700 | * | 11/1998 |

OTHER PUBLICATIONS

Patent Abstracts of Japan and Derwent World Patents Index English language abstracts for Japanese Patent No. 10295700, Nov. 10, 1998.
Patent Abstracts of Japan and Derwent World Patents Index English language abstracts for Japanese Patent No. 8275952, Oct. 22, 1996.
Patent Abstracts of Japan and Derwent World Patents Index English language abstracts for Japanese Patent No. 7–255736, Oct. 9, 1995.

* cited by examiner

*Primary Examiner*—Danny Worrell
(74) *Attorney, Agent, or Firm*—Barry R. Lipsitz; Douglas M. McAllister (57) ABSTRACT

The purpose of the present invention is to eliminate the various problems which can be presented by the scalpel portion of an ultrasonic hand piece for cutting a bone or other hard tissue making an excessive sting into the cut site, and allow precisely controlling the movement of the scalpel portion in a wide field of view for precision cutting of a bone or other hard tissue to achieve the purpose of the medical treatment.

The ultrasonic hand piece according to the present invention comprises a casing for accommodating an ultrasonic vibration mechanism, and a horn which is mounted at one end of the casing for cutting a bone or other hard tissue by the vibration transmitted from said ultrasonic vibration mechanism, said horn comprising a main body portion and a scalpel portion which is formed at the tip of this main body portion for cutting a bone or other hard tissue, and in the end portion of the scalpel portion being formed a working portion which comprises at least one face portion for eliminating the stress concentration into the object site of a bone or other hard tissue to prevent excessive sting while transmitting a vibration for forming a finely fractured layer, and an edge portion for raking the bone tissue finely fractured by this working portion.

18 Claims, 11 Drawing Sheets

(PRIOR ART)

Fig. 10

(PRIOR ART)

Fig. 11

(PRIOR ART)

ULTRASONIC HAND PIECE AND ULTRASONIC HORN FOR USE WITH THE SAME

BACKGROUND OF THE INVENTION

The present invention relates to an ultrasonic hand piece to be used for cutting a bone in the living body operation and an ultrasonic horn for use with the same.

In the medical treatment field, a number of ultrasonic hand pieces have been used as one of the variety of operation instruments in the surgical field.

Figure 9:
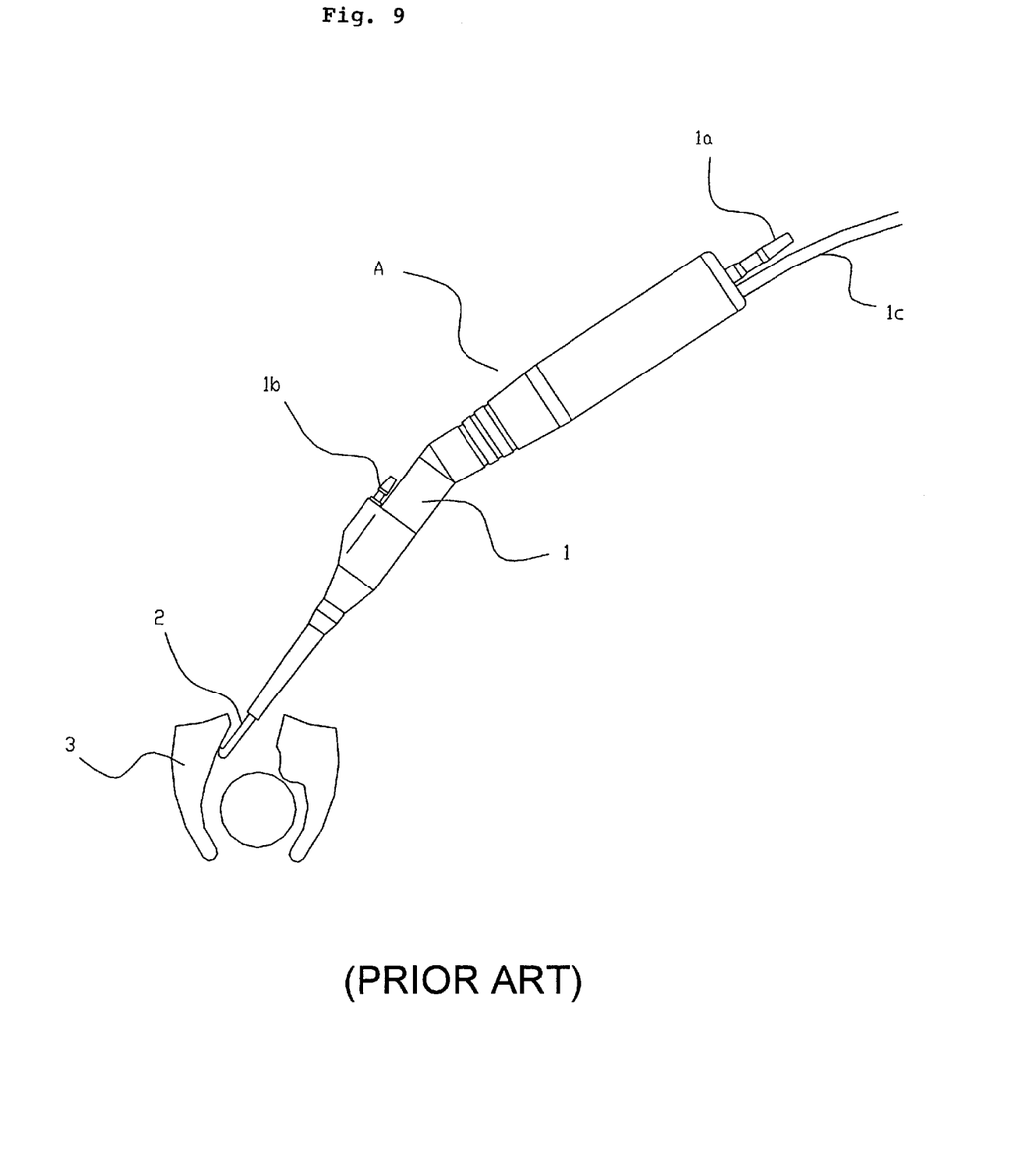
FIG. 9 is a side view showing a conventional ultrasonic hand piece.

FIG. 9 is a drawing showing an ultrasonic hand piece A to be used specifically for cutting a bone among such ultrasonic hand pieces.

In the figure, 1 denotes a casing for accommodating an ultrasonic vibration mechanism which is equipped with a vibrator of magnetostriction type, electrostriction type, or other type, and outputs an ultrasonic wave at the specified frequency; 2 a horn which is inserted into an opening portion at one end of the casing for cutting a bone or other tissue 3 with its end portion by the vibration transmitted from said ultrasonic vibration mechanism; 1a a joint for a tube for sucking the irrigation fluid, the cut debris, and the like; 1b a joint for a tube for injecting the irrigation fluid to cool the friction heat generated in cutting the bone; and 1c a cable for supplying high-frequency electric energy to said ultrasonic vibration mechanism.

By the vibration transmitted from the ultrasonic vibration mechanism, the horn 2 is vibrated at the specified frequency in the axial direction, and with the tip contacting the bone or other tissue 3, cuts the required site.

Figure 10:
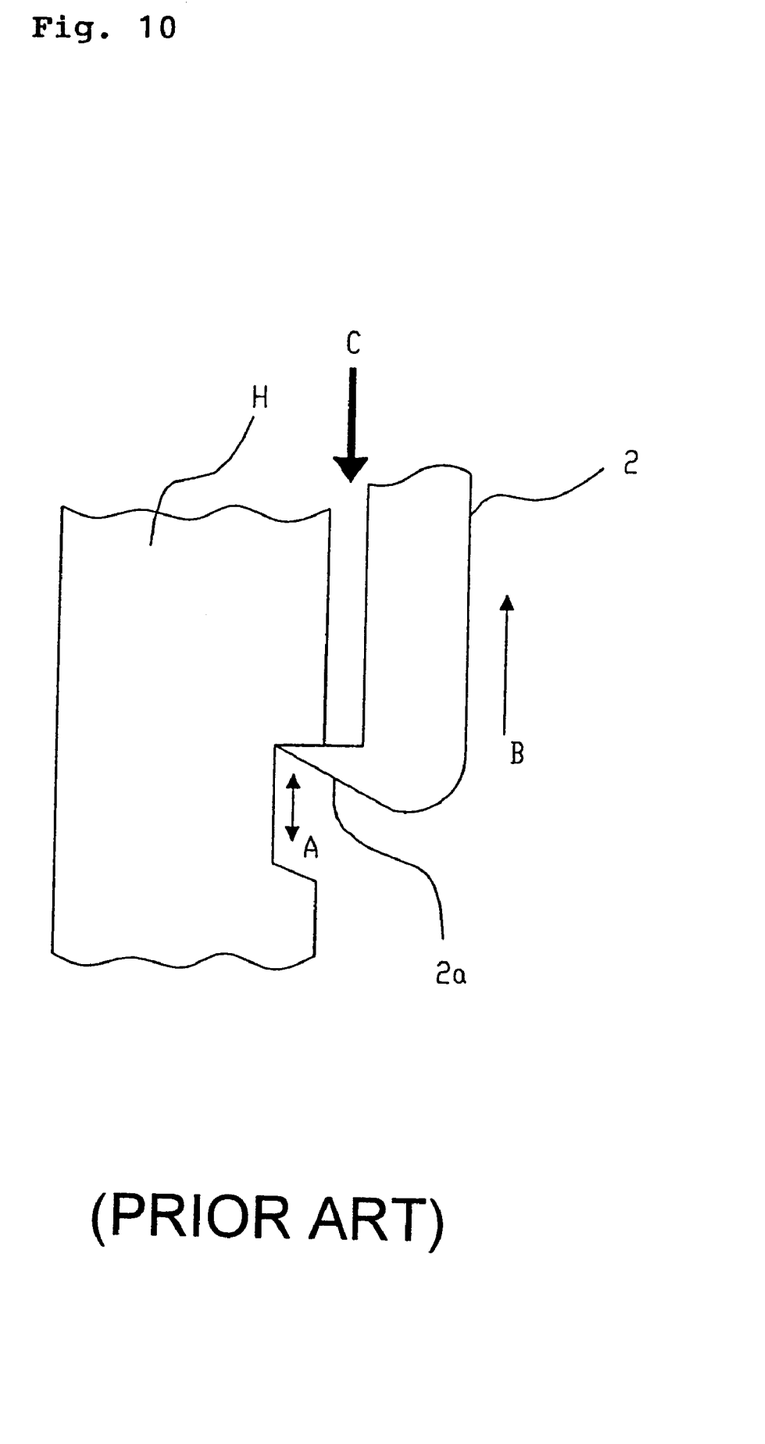
FIG. 10 is a sectional view showing the state of cutting a bone with a conventional ultrasonic horn.
Figure 11:
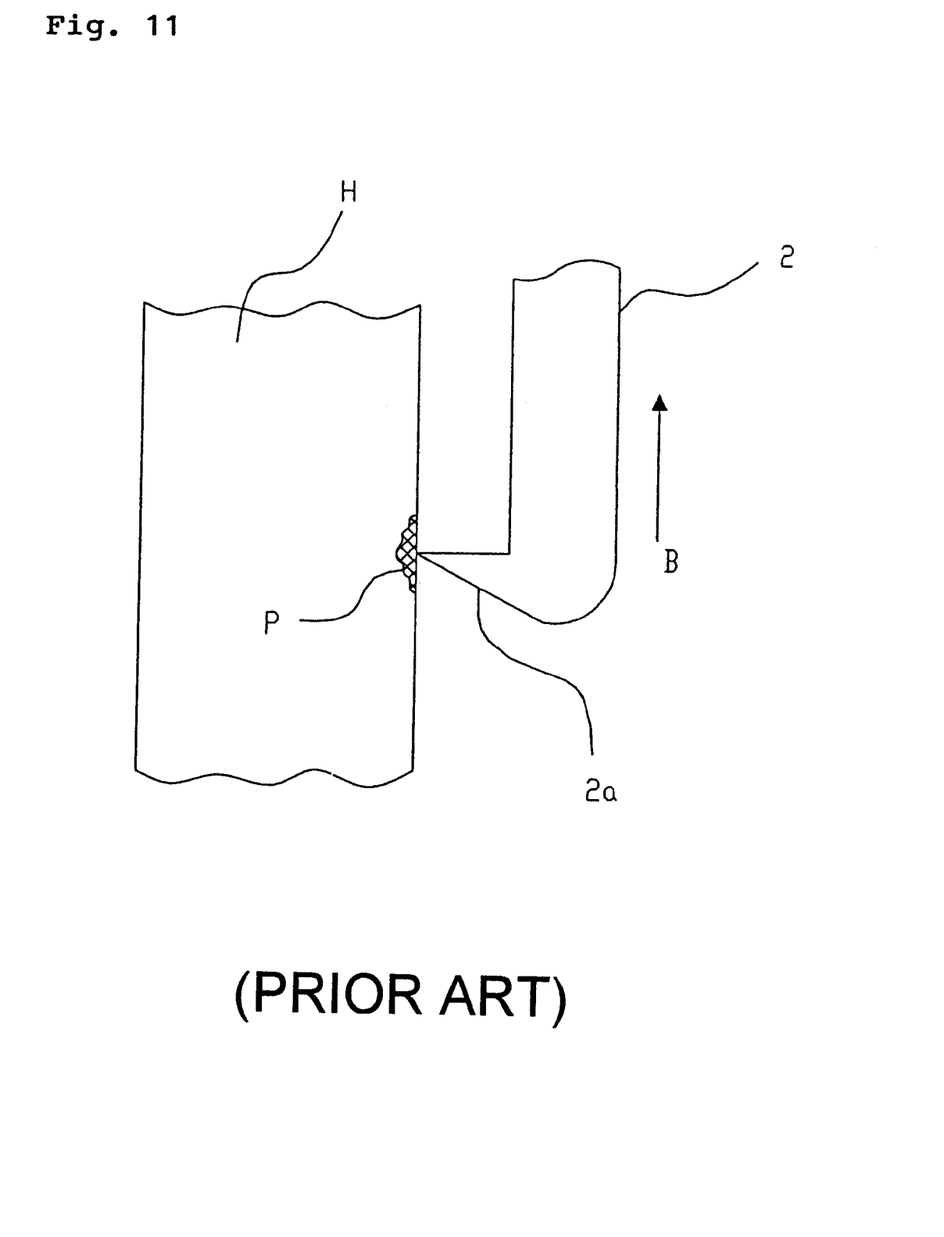
FIG. 11 is an explanatory drawing showing the state of forming a finely fractured layer with a conventional ultrasonic horn.

FIG. 10 is a figure showing the cutting operation on a bone or other hard tissue with the horn in said ultrasonic hand piece A. At the tip of the horn 2, a hook-shaped scalpel portion 2a is formed, and the operator operates the ultrasonic hand piece A from the direction of view indicated with the arrow C to move the horn 2 in the direction of the arrow B, while carrying out the cutting of the required site of the bone or other hard tissue with the tip of the scalpel portion 2a which is reciprocated in the direction of the arrow A. In such cutting, the vibration from the tip of the scalpel portion 2a is transmitted to the portion P of the bone or other hard tissue H opposing to the tip for finely fracturing it as shown in FIG. 11, and then, the finely fractured portion is raked with the tip of the scalpel portion 2a.

However, the tip of the scalpel portion 2a is finely vibrated at a rate of 25,000 cycles/sec with a stroke of 200 μm, thus the speed of the tip is 50 km/h at maximum.

Therefore, stresses are concentrated into the contacting portion of the sharply formed tip, which often causes the tip of the scalpel portion 2a to deeply penetrate into the tissue inside. If the tip deeply cuts into the tissue inside in this way, the bone is cut in quantity at a time, which not only requires a large amount of ultrasonic vibrational energy, but also requires the operator to exert a large force for operating the scalpel portion. In addition, because the tip of the scalpel portion tends to sting into the bone, there occurs a problem of that precise control of the amount of cut is difficult.

With the above-mentioned prior art, the scalpel portion is protruded at right angles to the horn main body, thus, as shown in FIG. 10, it is inevitable that the horn is positioned approximately in parallel to the surface of the bone H in operation, and thus the operator has been forced to make operation in an extremely narrow field of view in the direction of the arrow C.

Further, the above-mentioned prior art has presented a problem of that, if the scalpel portion is contacted with a site where water is collected, the water is atomized by the vibration, which hinders the sight of the operator. In addition, when cutting the bone and fracturing and sucking the tumor produced around it are alternatively performed, it has been conventionally required to prepare a hand piece for bone cutting and that for tumor fracturing and sucking, and to use either of them as needed.

SUMMARY OF THE INVENTION

The present invention is intended to solve the above mentioned conventional problems by providing an ultrasonic hand piece comprising an ultrasonic vibration mechanism which outputs a longitudinal ultrasonic vibration, a twisted ultrasonic vibration, or a compounded longitudinal and twisted ultrasonic vibration, a casing for accommodating the ultrasonic vibration mechanism, and a horn which is mounted at one end of the casing for cutting a bone or other hard tissue by the vibration transmitted from said ultrasonic vibration mechanism, wherein said horn comprises a main body portion and a scalpel portion which is formed at the tip of the main body portion for cutting a bone or other hard tissue, and in the end portion of the scalpel portion is formed a working portion which comprises at least one face portion for eliminating the stress concentration into the object site of a bone or other hard tissue to prevent excessive sting while transmitting a vibration for forming a finely fractured layer, and an edge portion for raking the bone tissue finely fractured by the working portion.

With the above-stated configuration, said scalpel portion may be formed in a hook-like shape so as to protrude from the main body portion side wall at the tip of the main body portion.

In addition, with the above-stated configuration, the angle of aperture for the hook-shaped scalpel with respect to the horn main body portion may be set in the range where the included angle between the internal side of the hook-shaped scalpel and the main body portion side wall is larger than a right angle and smaller than two right angles, so that a sufficient field of view for the operator can be secured between the cut portion and the main body portion.

Further, with the above-stated ultrasonic hand piece, an engaging portion to prevent sliding in contact with a bone or other hard tissue may be formed in the working portion at the tip of the scalpel portion.

In addition, with the above-stated ultrasonic hand piece, the outline portion of the hook-shaped scalpel portion may be formed in a curved shape in section, i.e., an approximately arc shape in section so that a receiving portion for cut bone tissue is formed between the main body portion and the scalpel portion for facilitating the cutting operation.

The present invention is also intended to solve the above mentioned conventional problems by constituting the ultrasonic horn for cutting a bone or other hard tissue by the vibration transmitted from an ultrasonic vibration source with a main body portion and a scalpel portion which is formed at the tip of the main body portion for cutting a bone or other hard tissue, and in the end portion of the scalpel portion, forming a working portion which comprises at least one face portion for eliminating the stress concentration into the object site of a bone or other hard tissue to prevent excessive sting while transmitting a vibration for forming a finely fractured layer, and an edge portion for raking the bone tissue finely fractured by the working portion.

With said ultrasonic horn, said scalpel portion may be formed in a hook-like shape so as to protrude from the main body portion side wall at the tip of the main body portion.

In addition, with the above-stated ultrasonic horn, the angle of aperture for the hook-shaped scalpel with respect to the horn main body portion may be set in the range where the included angle between the internal side of the hook-shaped scalpel and the main body portion side wall is larger than a right angle and smaller than two right angles, so that a sufficient field of view for the operator can be secured between the cut portion and the main body portion.

Further, with the above-stated ultrasonic horn, an engaging portion to prevent sliding in contact with a bone or other hard tissue may be formed in the working portion at the tip of the scalpel portion.

Still further, the outline portion of the hook-shaped scalpel portion may be formed in a curved shape in section, i.e., an approximately arc shape in section so that a receiving portion for cut bone tissue is formed between the main body portion and the scalpel portion.

And further, with the above-stated ultrasonic hand piece or ultrasonic horn, a suction passage is formed which, starting from one or more opening portions provided in the vicinity of the scalpel portion of the ultrasonic horn, runs through the horn main body portion to be connected to the suction mechanism, facilitating the suction and discharge of the water, the cut debris, the fracture debris, and the like in the operation site for allowing the proper and efficient operation.

With the present invention, the above-described configurations allow the following effects to be expected.
(1) The various problems which can be presented by the scalpel portion of an ultrasonic hand piece making an excessive sting into the cut site can be eliminated, and the movement of the scalpel portion can be precisely controlled, which allows precision cutting of a bone or other hard tissue to achieve the purpose of the medical treatment.
(2) The operator can always grasp the cutting situation in a wide field of view, which allows the operation to be made with safety and ease.

DETAILED DESCRIPTION OF THE INVENTION

Hereinafter, embodiments of the present invention will be described. The ultrasonic horn which will be described in each of the following embodiments is a member of the ultrasonic hand piece A as shown in FIG. 9, however, the members other than the horn member are completely the same, thus, description of them will be omitted.

Figure 1:
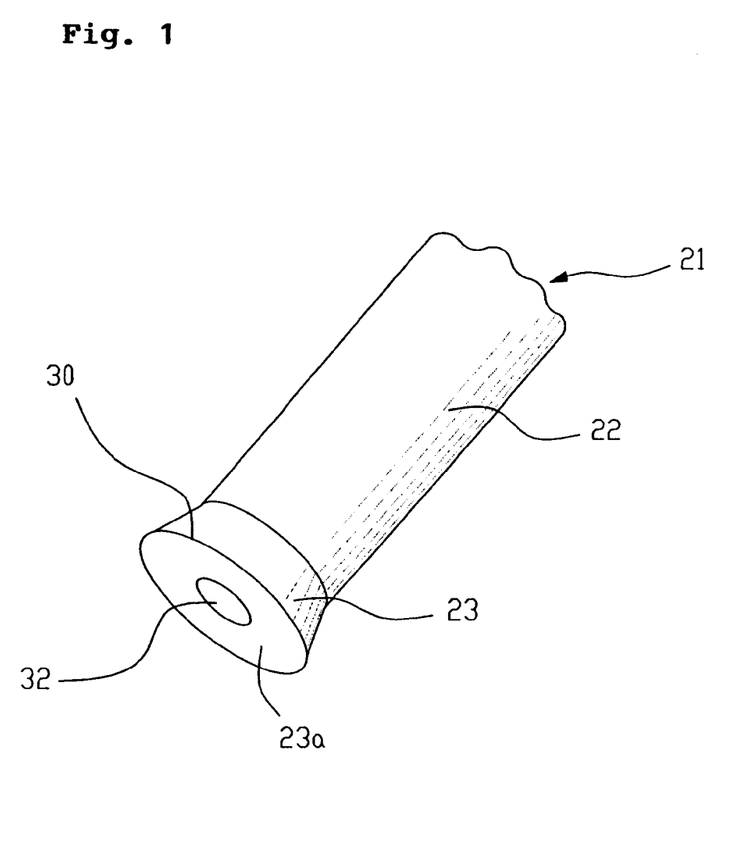
FIG. 1 is a perspective view showing an ultrasonic horn according to a first embodiment of the present invention.

FIG. 1 is a perspective view, with portions broken away for the sake of clarity, of an ultrasonic horn according to a first embodiment of the present invention, a horn 21 comprising a main body portion 22, and a scalpel portion 23 which is formed at the tip of this main body portion 22 for cutting a hard tissue, such as a bone, and at the tip of the scalpel portion 23, a working portion 23a being formed. This working portion 23a transmits a vibration to a bone or other hard tissue by contact to form a finely fractured layer, being configured as a flat face to diffuse the stresses imposed on the object site of a bone or other hard tissue for preventing the scalpel portion 23 from running into a bone or other hard tissue unnecessarily deeply.

At the peripheral edge of this working portion 23a configured as a flat face, an edge portion 30 is formed for raking the bone tissue finely fractured by vibration transmission, and making a desired cutting. In the working portion 23a, is formed an opening portion 32 for sucking and discharging the debris of a cut bone tissue and the like together with the irrigation fluid, being connected to the suction passage passing through the main body portion 22, which will be described in detail in an embodiment later described. In the present embodiment, the working portion 23a is circular, but being not limited to this shape, it may be square, hexagonal, octagonal or otherwise polygonal.

Further, with the present embodiment, the working portion 23a is configured as a flat face, however, because this working portion 23a is required to have a face portion as a means for preventing the stresses being concentrated into a point or line when being contacted with the tissue, the face may be curved or polyhedral as desired.

Figure 2:
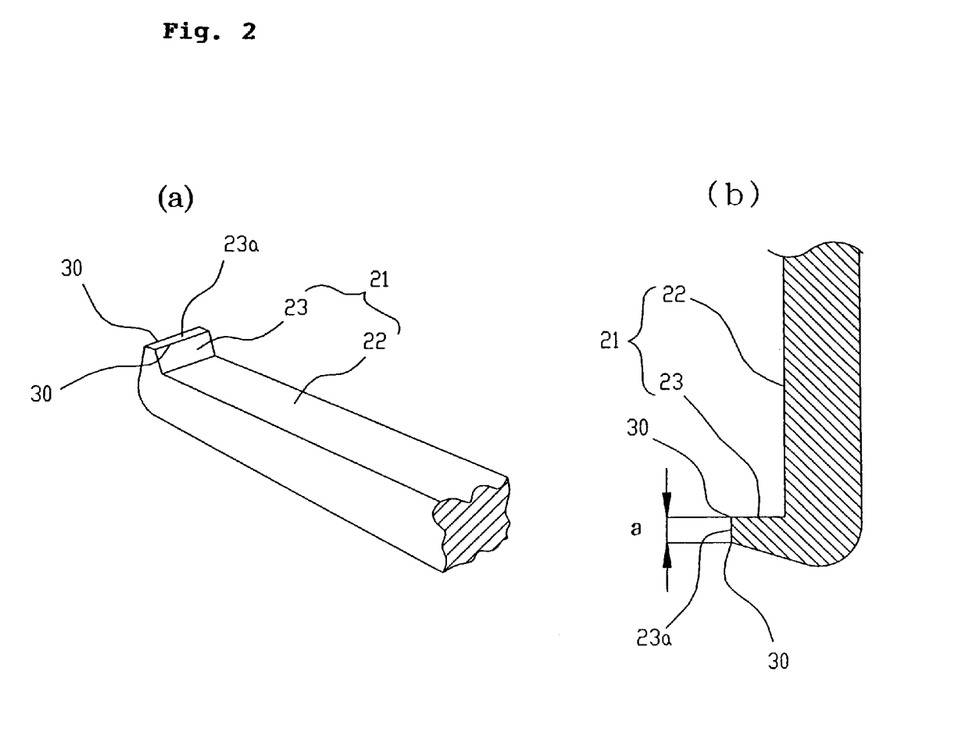
FIG. 2(a) and FIG. 2(b) are a perspective view and a sectional view showing an ultrasonic horn according to a second embodiment of the present invention.

FIG. 2(a) and FIG. 2(b) show the configuration of an ultrasonic horn according to a second embodiment of the present invention, FIG. 2(a) being a perspective view, with portions broken away for the sake of clarity, and FIG. 2(b) being a sectional view.

In these figures, 21 indicates an ultrasonic horn, which is loaded with its tip portion being protruded from the open end of the ultrasonic hand piece which is equipped with an ultrasonic vibration mechanism outputting ultrasonic waves at the specified frequency, and a casing or the like for accommodating this ultrasonic vibration mechanism, for cutting a hard tissue, such as a bone, with a vibration transmitted from said ultrasonic vibration mechanism.

This ultrasonic horn 21 comprises a main body portion 22 and a hook-shaped scalpel portion 23 which is formed so as to protrude from the main body portion side wall at the tip of the main body portion 22 for contacting with a living body tissue, and at the tip of the hookshaped scalpel portion 23; a working portion 23a for eliminating the stress concentration into the object site of a bone or other hard tissue to prevent excessive sting while transmitting a vibration for forming a finely fractured layer is formed; and at the peripheral edge of this working portion 23a configured as a flat face, an edge portion 30 is formed for raking the bone tissue finely fractured by vibration transmission, and making a desired cutting.

Thus, at the tip of the hook-shaped scalpel portion 23 contacting a bone or other hard tissue, a flat face as the working portion 23a is formed, therefore, unlike the prior art having a sharp tip, no stress concentration into a point or line is caused when the tip being contacted with a bone or other hard tissue, and an appropriate finely fractured layer in the cutting site of a bone or other hard tissue can be formed in the necessary range, with no problems resulting from the tip running too deeply into the bone or other hard tissue being presented.

Therefore, cutting operation can be made smoothly, and precise control can be performed.

Experiments show that, from the view point of such factors as cutting efficiency and operability, the thickness "a" of said flat portion 23a as shown in FIG. 2(b) should preferably be set at a value in the range of 0.5 mm<a<2.5 mm.

Figure 3:
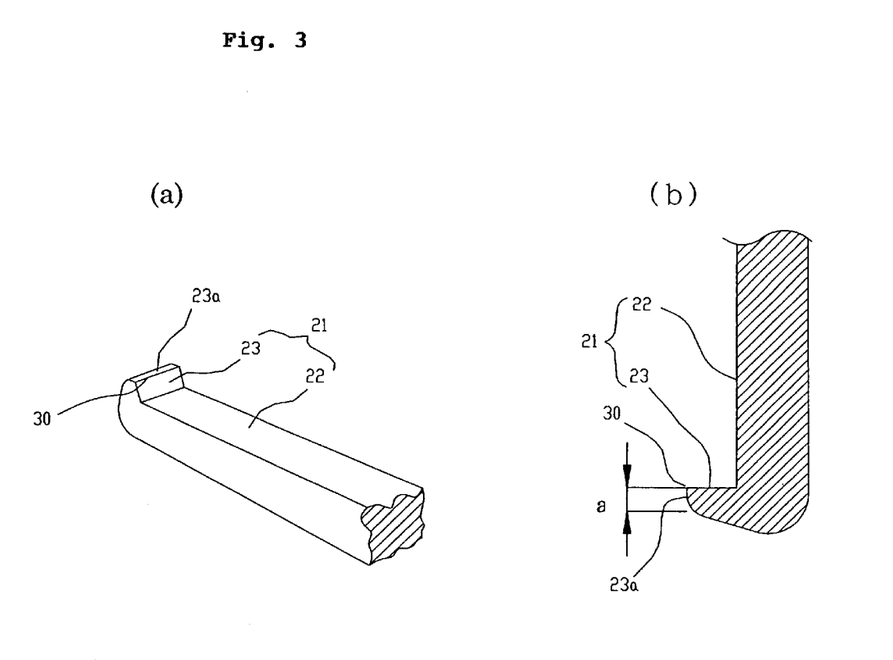
FIG. 3(a) and FIG. 3(b) are a perspective view and a sectional view showing an ultrasonic horn according to a third embodiment of the present invention.

FIG. 3(a) and FIG. 3(b) show the configuration of an ultrasonic horn according to a third embodiment of the present invention, FIG. 3(a) being a perspective view, with portions broken away for the sake of clarity, and FIG. 3(b) being a sectional view.

With the present embodiment, the tip of the hook-shaped scalpel portion 23 is formed in the shape of an arc in section, therefore, the working portion 23a is formed as a curved face, and at one end of the curved face is formed an edge portion 30 for raking the bone tissue from the finely fractured layer formed by vibration transmission from the working portion 23a. Thus, the working portion 23a has a face configuration, therefore, as with said each embodiment, no stress concentration into a point or line is caused when the tip being in contact with a bone or other hard tissue, and a finely fractured layer can be properly formed in the cutting site of a bone or other hard tissue in the necessary range, with no problems resulting from the tip running too deeply into the bone or other hard tissue being presented. Because the tip will not sting too deeply into the bone or other hard tissue, cutting operation can be made smoothly, and precise control can be performed.

As is the case with the above embodiment, experiments show that, from the view point of such factors as cutting efficiency and operability, the thickness of said arc portion 23a as the stress diffusion end portion, i.e., the thickness "a" of the portion opposed to the cut surface of the bone should preferably be set at a value in the range of 0.5 mm<a<2.5 mm.

Figure 4:
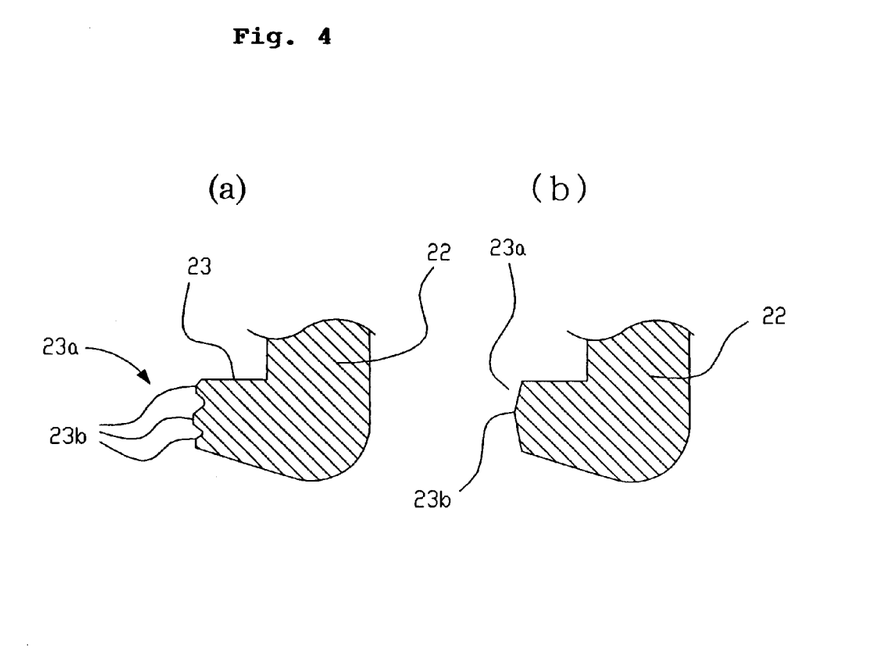
FIG. 4(a) and FIG. 4(b) are a sectional view showing the configuration of an ultrasonic horn according to a fourth embodiment of the present invention.

FIG. 4(a) and FIG. 4(b) are a sectional view showing the configuration of an ultrasonic horn according to a fourth embodiment of the present invention. With the present embodiment, in the face portion configuring the working portion 23a at the tip of the hookshaped scalpel portion 23, is formed an engaging portion to prevent sliding in contact with a bone or other hard tissue. FIG. 4(a) shows an application where a few curved surface ridges are formed as said engaging portion 23b in the working portion 23a.

FIG. 4(b) shows an application where a hill-like portion is formed as said engaging portion 23b. These engaging portions 23b can be formed in either of the stress diffusion end portions as shown in FIG. 1, FIG. 2(a) and FIG. 2(b).

By providing an engaging portion 23b in the working portion 23a, occurrence of an unexpected sliding at the tip of the hook-shaped scalpel portion 23 in cutting can be prevented, which allows more precise control of cutting. With these embodiments, an edge portion is formed at the periphery of the working portion 23a as with each of the above embodiments.

Figure 5:
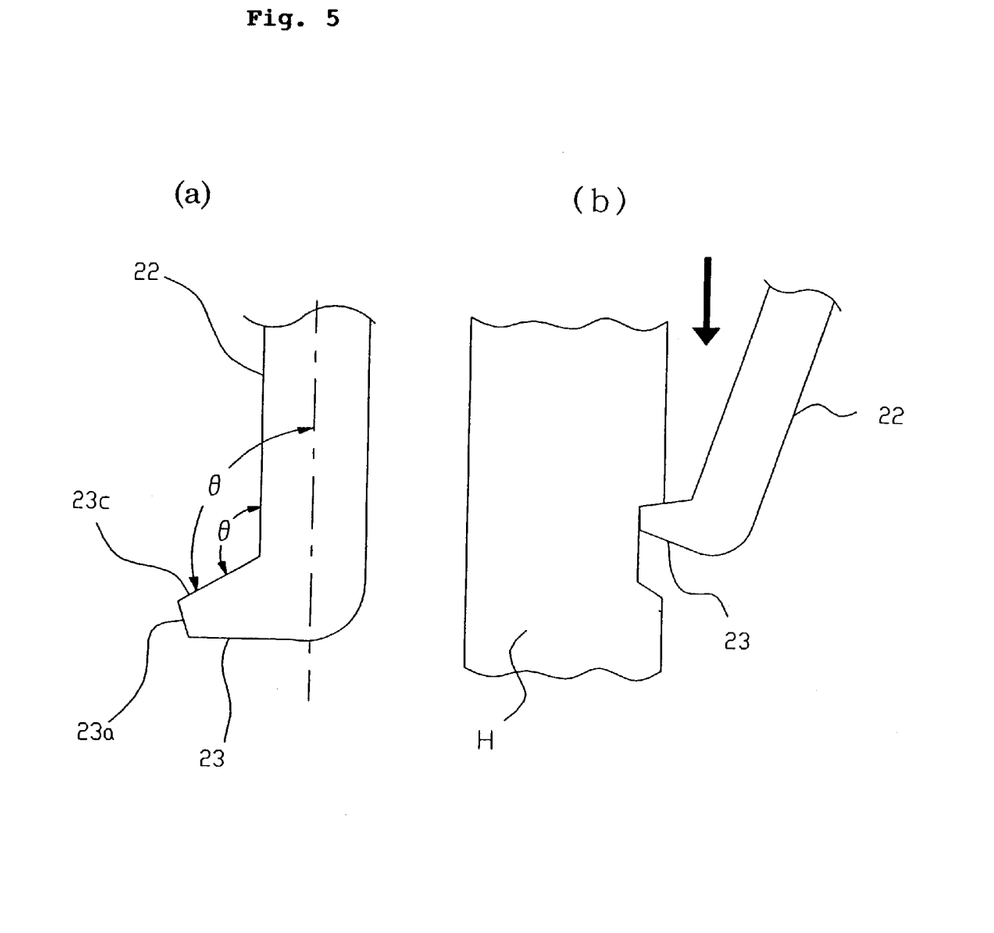
FIG. 5(a) and FIG. 5(b) are a sectional view showing an ultrasonic horn according to a fifth embodiment of the present invention.

FIG. 5 is a sectional view showing the configuration of an ultrasonic horn according to a fifth embodiment of the present invention. With the present embodiment, the angle of aperture, θ, for the hook-shaped scalpel portion 23 with respect to the horn main body portion 22 is set in the range where the included angle between the internal side of the hook-shaped scalpel and the main body portion side wall, or the included angle between the internal side of the hook-shaped scalpel and the axis of the main body portion is larger than a right angle and smaller than two right angles, so that a sufficient field of view for the operator can be secured between the cut portion and the main body portion.

In other words, as shown in FIG. 5(a), the included angle θ between the internal side 23c of the hook-shaped scalpel and the side wall of the main body portion 22 is set at approx. 120 deg.

Therefore, as shown in FIG. 5(b), the bone or other hard tissue H can be cut with the horn main body portion 22 being inclined, which allows the operator to secure a wide field of view as shown with an arrow for operation while checking for situation, resulting in more precise cutting being possible.

It is evident that the scheme for setting the angle of aperture for the hook-shaped scalpel portion 23 with respect to the horn main body portion 22 can be applicable to the ultrasonic horn as shown in FIG. 2(a) and FIG. 2(b) to FIG. 4(a) and FIG. 4(b). The schemes for the working portion and the edge portion are the same as those in each of the above embodiments.

Figure 6:
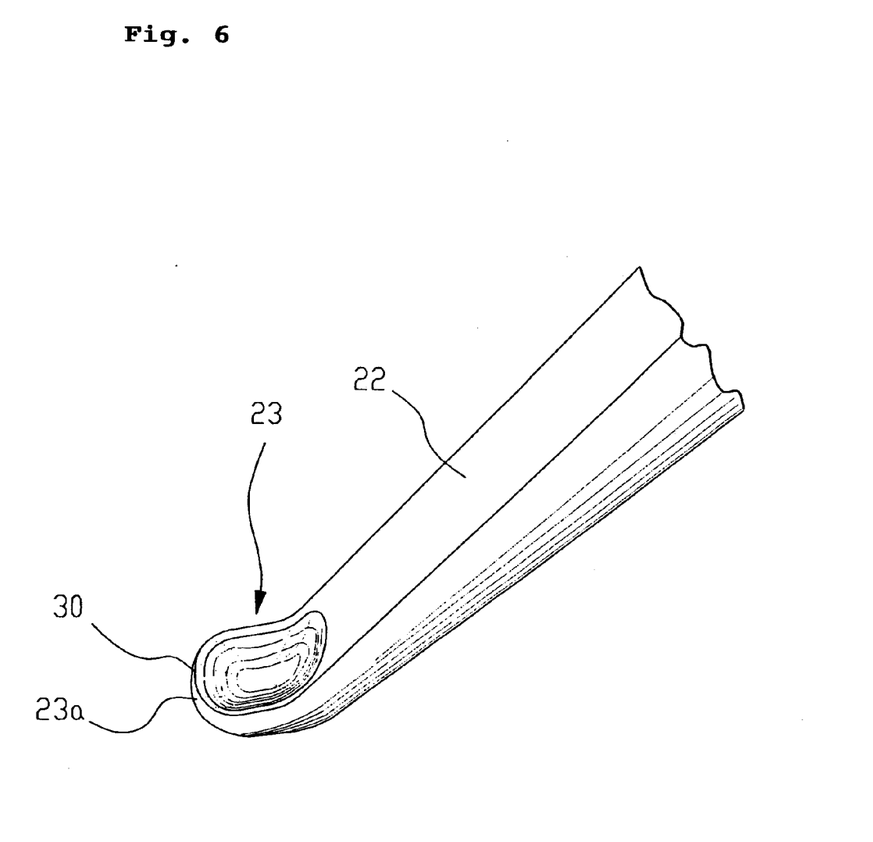
FIG. 6 is a perspective view showing an ultrasonic horn according to a sixth embodiment of the present invention.

FIG. 6 is a perspective view showing the configuration of an ultrasonic horn according to a sixth embodiment of the present invention. With the present embodiment, the hook-shaped scalpel portion 23 is formed in a spoon-like shape, the working portion 23a being formed as a curved face, and at the upper edge of this working portion 23a is formed an edge portion 30. The spoon recessed portion functions as a portion for receiving the cut debris, and by providing an opening portion connecting to the suction tube in this recessed portion, the irrigation fluid and the cut debris can be discharged with extreme ease.

Figure 7:
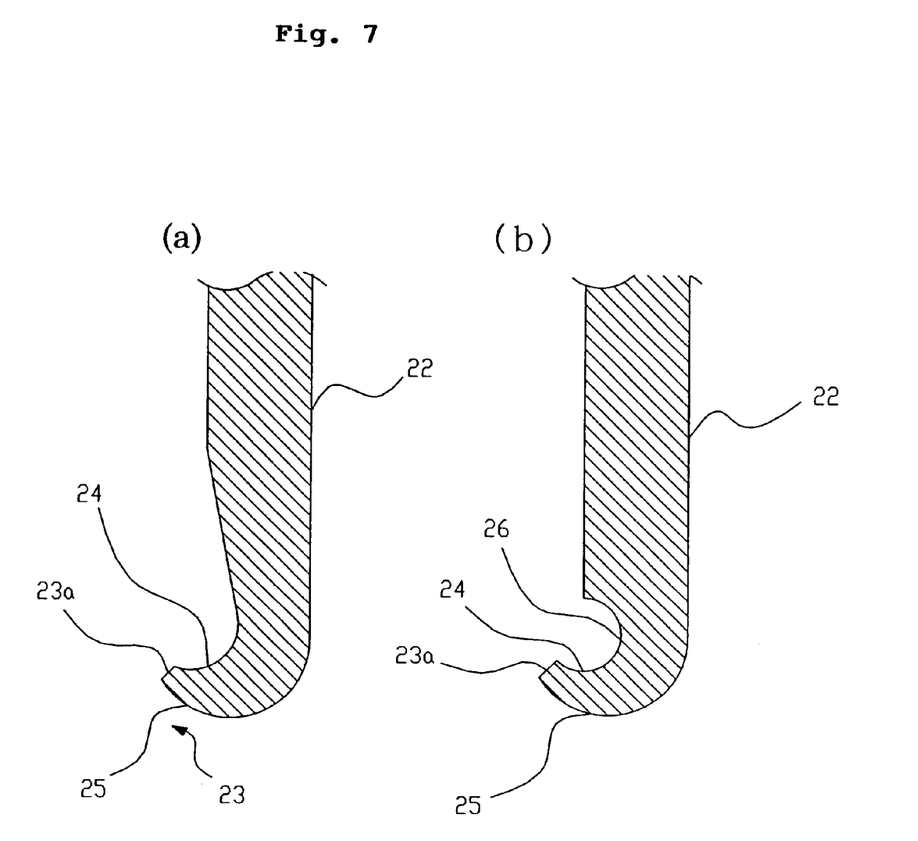
FIG. 7(a) and FIG. 7(b) are a sectional view showing an ultrasonic horn according to a seventh embodiment of the present invention.

FIG. 7(a) and FIG. 7(b) are a sectional view showing the configuration of an ultrasonic horn according to a seventh embodiment of the present invention. With the present embodiment, the outline portion in section of the hook-shaped scalpel portion 23 is formed in a curved line shape. In other words, with the ultrasonic horn as shown in FIG. 7(a), the hook-shaped scalpel portion 23 which is curved with curved lines being drawn is connectedly formed at the end portion of the horn main body portion 22 which is formed, being tapered. In other words, the upper surface portion 24 and the lower surface portion 25 of the hook-shaped scalpel portion 23 are formed as an arc curved surface having the specified diameter, respectively, and in the tip portion is formed a working portion 23a configured as one or more flat faces or curved faces, an edge portion being formed at the periphery. The working portion 23a may be provided with the above-mentioned engaging portion 23b when required.

With the ultrasonic horn as shown in FIG. 7(b), the hook-shaped scalpel portion 23 is formed in an approximately arc shape in section so that a cutout portion is formed in the inside end portion (the portion opposing the bone) of the horn main body portion 22. In other words, the upper surface portion 24 and the lower surface portion 25 of the hook-shaped scalpel portion 23 are formed as an arc curved surface having the specified diameter, respectively, as in the above FIG. 7(a), and in the tip portion is formed a working portion 23a configured as one or more flat faces or curved faces.

In FIG. 7(b), 26 indicates a cut debris receiving portion in a semi-circular shape in section formed at the inside end portion (the portion opposing the bone) of the horn main body portion 22, to which the cut debris raked by the edge portion 30 from the finely fractured portion is led.

Also in this case, the above-mentioned engaging portion 23b is formed in the working portion 23a as required. With the embodiments as shown in FIG. 7(a) and FIG. 7(b), the hook-shaped scalpel portion 23 adopts the above-stated configuration, and thus the operator can use the ultrasonic horn, inclining it with respect to the cut surface of the bone, as with the case as shown in FIG. 5(b), in cutting a bone or other hard tissue, thus obtaining a wide field of view.

Figure 8:
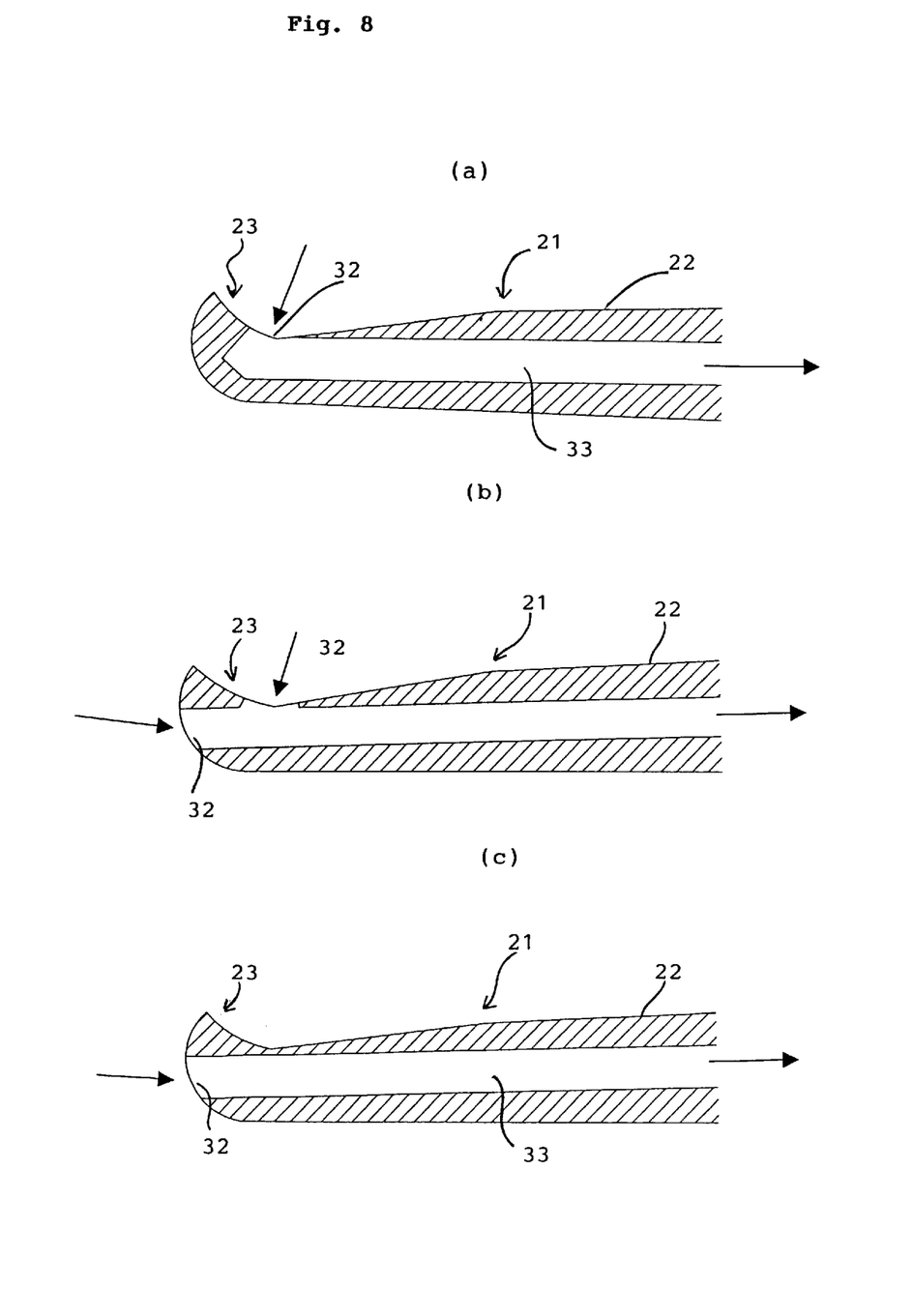
FIG. 8(a) to FIG. 8(c) are a sectional view showing an ultrasonic horn according to an eighth embodiment of the present invention.

FIG. 8(a) to FIG. 8(c) are a sectional view showing the configuration of an ultrasonic horn according to an eighth embodiment of the present invention. With the present embodiment, one or more opening portions are provided in the vicinity of the scalpel portion of the ultrasonic horn as shown in FIG. 6, and a suction passage is formed which, starting from such opening portion, runs through the horn main body portion to be connected to the suction mechanism, facilitating the suction and discharge of the water, the cut debris, the fracture debris, and the like in the operation site for realization of the proper and efficient operation.

In FIG. 8(a), 33 indicates a suction passage which penetrates through the horn main body portion 22 to be connected to the suction mechanism (not shown), having an opening portion 32 in the vicinity and inside of the scalpel portion 23.

With the ultrasonic horn as shown in FIG. 8(b), the suction passage has two opening portions 32, one of which is formed in the same place as that shown in FIG. 8(a), and the other of which is formed at the tip of the horn main body portion 22 in the vicinity and outside of the scalpel portion 23. With the ultrasonic horn as shown in FIG. 8(c), the opening portion 32 of the suction passage 33 is formed at the tip of the horn main body portion 22 in the vicinity and outside of the scalpel portion 23.

The water, the cut debris, the fracture debris, and the like in the operation site are sucked at the opening portion 32, and discharged through the suction passage 33.

With the present invention, the working portion is designed to avoid the concentration of the vibrational energy into a single point or line when being contacted with a bone or other hard tissue, and thus eliminate the problem resulting from the unnecessary spread of the finely fractured layer in the direction of the depth.

Therefore, to provide the above function, the working portion is necessarily equipped with a face, which may comprise only a single face or a plurality of faces, and be flat or curved, if the energy can be distributed and transmitted.

What is claimed is:

1. An ultrasonic hand piece comprising an ultrasonic vibration mechanism which outputs a longitudinal ultrasonic vibration, a twisted ultrasonic vibration, or a compounded longitudinal and twisted ultrasonic vibration, a casing for accommodating the ultrasonic vibration mechanism, and a horn which is mounted at one end of the casing for amplifying the vibration transmitted from said ultrasonic vibration mechanism,
   wherein said horn comprises a main body portion and a scalpel portion which is formed at a tip of the main body portion for cutting a bone or other hard tissue, and in an end portion of the scalpel portion is formed a working portion which comprises at least one face portion having at least one ridged engaging portion to prevent sliding of said scalpel portion on contact with a bone or other hard tissue, and an edge portion for raking the bone tissue finely fractured by the working portion.

2. An ultrasonic hand piece according to claim 1, wherein said scalpel portion protrudes from the main body portion side wall at the tip of the main body portion.

3. An ultrasonic hand piece according to claim 2, wherein the angle of aperture for the scalpel with respect to the horn main body portion is set in the range where the included angle between the internal side of the scalpel and the main body portion side wall is larger than 90 degrees and smaller than 180 degrees, so that a sufficient field of view for the operator can be secured between the cut portion and the main body portion.

4. An ultrasonic hand piece according to claim 2, wherein the scalpel portion is formed in an approximately arc shape in section so that a receiving portion for cut bone tissue is formed between the main body portion and the scalpel portion.

5. An ultrasonic hand piece according to claim 3, wherein the scalpel portion is formed in an approximately arc shape in section so that a receiving portion for cut bone tissue is formed between the main body portion and the scalpel portion.

6. An ultrasonic horn for cutting a bone or other hard tissue by the vibration transmitted from an ultrasonic vibration source,
   wherein said horn comprises a main body portion and a scalpel portion which is formed at a tip of the main body portion for cutting a bone or other hard tissue, and in an end portion of the scalpel portion is formed a working portion which comprises at least one face portion having at least one ridged engaging portion to prevent sliding of said scalpel portion on contact with a bone or other hard tissue, and an edge portion for raking the bone tissue finely fractured by the working portion.

7. An ultrasonic horn according to claim 6, wherein said scalpel portion protrudes from the main body portion side wall at the tip of the main body portion.

8. An ultrasonic horn according to claim 6, wherein the angle of aperture for the scalpel with respect to the horn main body portion is set in the range where the included angle between the internal side of the scalpel and the main body portion side wall is larger than 90 degrees and smaller than 180 degrees, so that a sufficient field of view for the operator can be secured between the cut portion and the main body portion.

9. An ultrasonic horn according to claim 7, wherein the scalpel portion is formed in an approximately arc shape in section so that a receiving portion for cut bone tissue is formed between the main body portion and the scalpel portion.

10. An ultrasonic horn according to claim 8, wherein the scalpel portion is formed in an approximately arc shape in section so that a receiving portion for cut bone tissue is formed between the main body portion and the scalpel portion.

11. An ultrasonic hand piece according to claim 1, further comprising a suction passage which starts from one or more opening portions formed in the vicinity of the scalpel portion, running through the horn main body portion to be connected to a suction mechanism.

12. An ultrasonic hand piece according to claim 2, further comprising a suction passage which starts from one or more opening portions formed in the vicinity of the scalpel portion, running through the horn main body portion to be connected to a suction mechanism.

13. An ultrasonic hand piece according to claim 3, further comprising a suction passage which starts from one or more opening portions formed in the vicinity of the scalpel portion, running through the horn main body portion to be connected to a suction mechanism.

14. An ultrasonic hand piece according to claim 4, further comprising a suction passage which starts from one or more opening portions formed in the vicinity of the scalpel portion, running through the horn main body portion to be connected to a suction mechanism.

15. An ultrasonic horn according to claim 6, further comprising a suction passage which starts from one or more opening portions formed in the vicinity of the scalpel portion, running through the horn main body portion to be connected to a suction mechanism.

16. An ultrasonic horn according to claim 7, further comprising a suction passage which starts from one or more opening portions formed in the vicinity of the scalpel portion, running through the horn main body portion to be connected to a suction mechanism.

17. An ultrasonic horn according to claim 8, further comprising a suction passage which starts from one or more opening portions formed in the vicinity of the scalpel portion, running through the horn main body portion to be connected to a suction mechanism.

18. An ultrasonic horn according to claim 9, further comprising a suction passage which starts from one or more opening portions formed in the vicinity of the scalpel portion, running through the horn main body portion to be connected to a suction mechanism.

* * * * *

US006497715C1

(12) EX PARTE REEXAMINATION CERTIFICATE (10800th)
United States Patent
Satou (10) Number: US 6,497,715 C1
(45) Certificate Issued: Feb. 1, 2016

(54) ULTRASONIC HAND PIECE AND ULTRASONIC HORN FOR USE WITH THE SAME

(75) Inventor: Yuichirou Satou, Kawasaki (JP)

(73) Assignee: Stryker Corporation

Reexamination Request:
No. 90/013,403, Nov. 19, 2014

Reexamination Certificate for:
Patent No.: 6,497,715
Issued: Dec. 24, 2002
Appl. No.: 09/802,813
Filed: Mar. 9, 2001

(30) Foreign Application Priority Data

Nov. 7, 2000 (JP) .................................. 2000-338488

(51) Int. Cl.
*A61B 17/32* (2006.01)

(52) U.S. Cl.
CPC .................... *A61B 17/320068* (2013.01); *A61B 2017/320072* (2013.01)

(58) Field of Classification Search
None
See application file for complete search history.

(56) References Cited

To view the complete listing of prior art documents cited during the proceeding for Reexamination Control Number 90/013,403, please refer to the USPTO's public Patent Application Information Retrieval (PAIR) system under the Display References tab.

*Primary Examiner* — Patricia Engle

(57) ABSTRACT

The purpose of the present invention is to eliminate the various problems which can be presented by the scalpel portion of an ultrasonic hand piece for cutting a bone or other hard tissue making an excessive sting into the cut site, and allow precisely controlling the movement of the scalpel portion in a wide field of view for precision cutting of a bone or other hard tissue to achieve the purpose of the medical treatment.

The ultrasonic hand piece according to the present invention comprises a casing for accommodating an ultrasonic vibration mechanism, and a horn which is mounted at one end of the casing for cutting a bone or other hard tissue by the vibration transmitted from said ultrasonic vibration mechanism, said horn comprising a main body portion and a scalpel portion which is formed at the tip of this main body portion for cutting a bone or other hard tissue, and in the end portion of the scalpel portion being formed a working portion which comprises at least one face portion for eliminating the stress concentration into the object site of a bone or other hard tissue to prevent excessive sting while transmitting a vibration for forming a finely fractured layer, and an edge portion for raking the bone tissue finely fractured by this working portion.

(a)

(b)

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 8 and 17 are cancelled.

Claims 1 and 6 are determined to be patentable as amended.

Claims 2, 3, 7, 11-13, 15 and 16, dependent on an amended claim, are determined to be patentable.

New claims 19-27 are added and determined to be patentable.

Claims 4, 5, 9, 10, 14 and 18 were not reexamined.

1. An ultrasonic hand piece comprising an ultrasonic vibration mechanism [which outputs a longitudinal ultrasonic vibration], *wherein the ultrasonic hand piece, in conjunction with the ultrasonic vibration mechanism, yields* a twisted ultrasonic vibration[.] *or a compounded longitudinal and twisted ultrasonic vibration,* a casing for accommodating the ultrasonic vibration mechanism, and a horn which is mounted at one end of the casing for amplifying the vibration transmitted from said ultrasonic vibration mechanism, wherein said horn comprises a main body portion and a scalpel portion which is formed at a tip of the main body portion for cutting a bone or other hard tissue, and in an end portion of the scalpel portion is formed a working portion which comprises at least one face portion having at least one ridged engaging portion to prevent sliding of said scalpel portion on contact with a bone or other hard tissue, and an edge portion for raking the bone tissue finely fractured by the working portion.

6. An ultrasonic horn for cutting a bone or other hard tissue by the vibration transmitted from an ultrasonic vibration source, wherein said horn comprises a main body portion and a scalpel portion which is formed at a tip of the main body portion for cutting a bone or other hard tissue, and in an end portion of the scalpel portion is formed a working portion which comprises at least one face portion having at least one ridged engaging portion to prevent sliding of said scalpel portion on contact with a bone or other hard tissue, and an edge portion for raking the bone tissue finely fractured by the working portion,

*wherein a thickness of said working portion is between 0.5 mm and 2.5 mm, and*

*wherein the angle of aperture for the scalpel with respect to the horn main body portion is set in the range where the included angle between the internal side of the scalpel and the main body portion side wall is larger than 90 degrees and smaller than 180 degrees, so that a sufficient field of view for the operator can be secured between the cut portion and the main body portion.*

*19. An ultrasonic hand piece according to claim 1, wherein a thickness of said working portion is between 0.5 mm and 2.5 mm.*

*20. An ultrasonic hand piece according to claim 1, wherein said scalpel portion is formed in a hook-like shape.*

*21. An ultrasonic hand piece according to claim 1, wherein said scalpel portion is formed in a spoon-like shape.*

*22. An ultrasonic horn according to claim 6, wherein said scalpel portion is formed in a hook-like shape.*

*23. An ultrasonic horn according to claim 6, wherein said scalpel portion is formed in a spoon-like shape.*

*24. An ultrasonic hand piece comprising:*

*an ultrasonic vibration mechanism that outputs at least one of a longitudinal ultrasonic vibration, a twisted ultrasonic vibration, and a compounded longitudinal and twisted ultrasonic vibration;*

*a casing for accommodating the ultrasonic vibration mechanism; and*

*a horn mounted at one end of the casing for amplifying the vibration transmitted from said ultrasonic vibration mechanism,*

*wherein said horn comprises a main body portion and a scalpel portion, which is formed at a tip of the main body portion for cutting a bone or other hard tissue, and in an end portion of the scalpel portion is formed a working portion that comprises at least one face portion having at least one ridged engaging portion to prevent sliding of said scalpel portion on contact with a bone or other hard tissue, and an edge portion for raking the bone tissue finely fractured by the working portion,*

*wherein a thickness of said working portion is between 0.5 mm and 2.5 mm.*

*25. An ultrasonic hand piece according to claim 24, wherein the angle of aperture for the scalpel with respect to the horn main body portion is set in the range where the included angle between the internal side of the scalpel and the main body portion side wall is larger than 90 degrees and smaller than 180 degrees, so that a sufficient field of view for the operator can be secured between the cut portion and the main body portion.*

*26. An ultrasonic hand piece according to claim 24, wherein the ultrasonic hand piece, in conjunction with the ultrasonic vibration mechanism, yields a twisted ultrasonic vibration.*

*27. An ultrasonic hand piece according to claim 24, wherein the ultrasonic hand piece, in conjunction with the ultrasonic vibration mechanism, yields a compounded longitudinal and twisted ultrasonic vibration.*

\* \* \* \* \*